US011583667B1

(12) United States Patent
Leeflang et al.

(10) Patent No.: US 11,583,667 B1
(45) Date of Patent: Feb. 21, 2023

(54) FLOW DISTRIBUTION PAD AND METHODS FOR USING THEM

(71) Applicant: AUST Development, LLC, Palo Alto, CA (US)

(72) Inventors: Stephen Arie Leeflang, Sunnyvale, CA (US); Christian Scott Eversull, Palo Alto, CA (US)

( * ) Notice: Subject to any disclaimer, the term of this patent is extended or adjusted under 35 U.S.C. 154(b) by 0 days.

(21) Appl. No.: 15/439,922

(22) Filed: Feb. 22, 2017

Related U.S. Application Data

(60) Provisional application No. 62/298,455, filed on Feb. 22, 2016.

(51) Int. Cl.
*A61M 35/00* (2006.01)
*A61M 31/00* (2006.01)
*A61M 1/00* (2006.01)

(52) U.S. Cl.
CPC .............. *A61M 35/00* (2013.01); *A61M 1/84* (2021.05); *A61M 31/00* (2013.01); *A61M 2202/048* (2013.01); *A61M 2205/0222* (2013.01)

(58) Field of Classification Search
CPC .... A61M 1/008; A61M 27/00; A61M 35/006; A61M 1/0058; A61M 1/0023
See application file for complete search history.

(56) References Cited

U.S. PATENT DOCUMENTS

| | | | | |
|---|---|---|---|---|
| 1,523,943 | A * | 1/1925 | Fowle | A61M 3/0279 604/1 |
| 5,151,094 | A * | 9/1992 | Hanifl | A61C 17/08 604/118 |
| 5,407,423 | A * | 4/1995 | Yoon | A61B 17/0281 604/11 |
| 6,283,931 | B1 * | 9/2001 | Augustine | A61F 7/007 602/14 |
| 6,290,685 | B1 * | 9/2001 | Insley | F28F 21/065 366/DIG. 3 |
| 7,781,639 | B2 * | 8/2010 | Johnston | A47L 9/02 602/42 |
| 2004/0265040 | A1 * | 12/2004 | Rosenberg | A61B 90/80 401/203 |
| 2005/0131327 | A1 * | 6/2005 | Lockwood | A61M 1/90 602/41 |
| 2007/0219497 | A1 * | 9/2007 | Johnson | A61M 27/00 604/131 |
| 2011/0159457 | A1 * | 6/2011 | Offermann | A61M 1/0068 433/91 |
| 2011/0166550 | A1 * | 7/2011 | Alexander | A61B 17/00234 606/1 |

(Continued)

*Primary Examiner* — William R Carpenter
(74) *Attorney, Agent, or Firm* — William A. English; Vista IP Law Group LLC

(57) ABSTRACT

Apparatus and methods are provided for delivering fluids into a patient's body that includes a tubular member including a proximal end, a distal end sized for introduction into a patient's body, and a fluid delivery lumen extending between the proximal and distal ends; and a flexible pad on the distal end including a tissue contacting surface, a passage communicating with the fluid delivery lumen, and plurality of capillary channels in the tissue contact surface communicating with the passage, the capillary channels configured to deliver fluid from the fluid delivery lumen and passage to tissue contacted by the tissue contact surface.

25 Claims, 2 Drawing Sheets

(56) References Cited

U.S. PATENT DOCUMENTS

2011/0213320 A1* 9/2011 Blott ................... A61M 35/00
  604/313
2013/0079590 A1* 3/2013 Bengtson .......... A61F 13/15268
  604/93.01

* cited by examiner

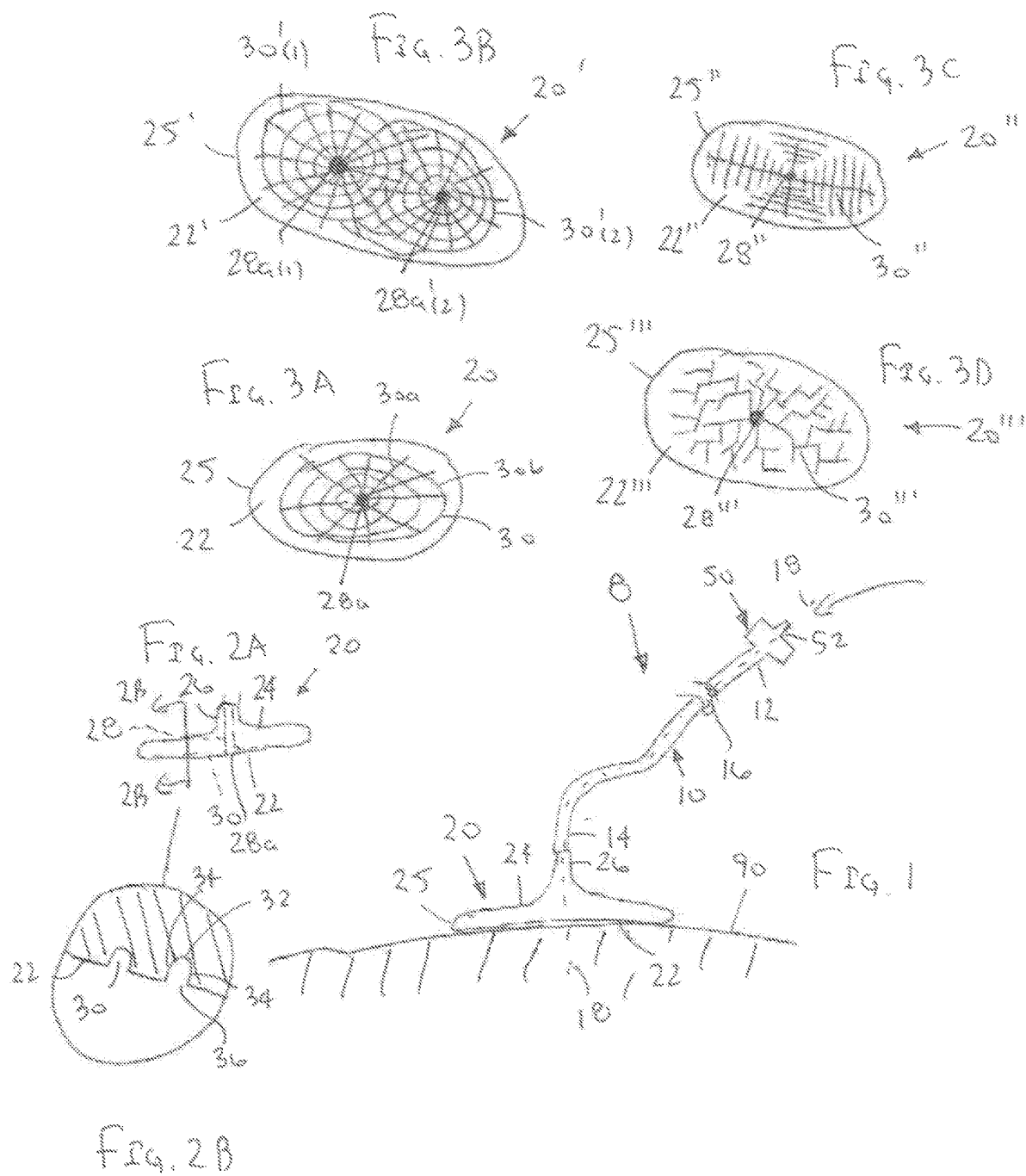

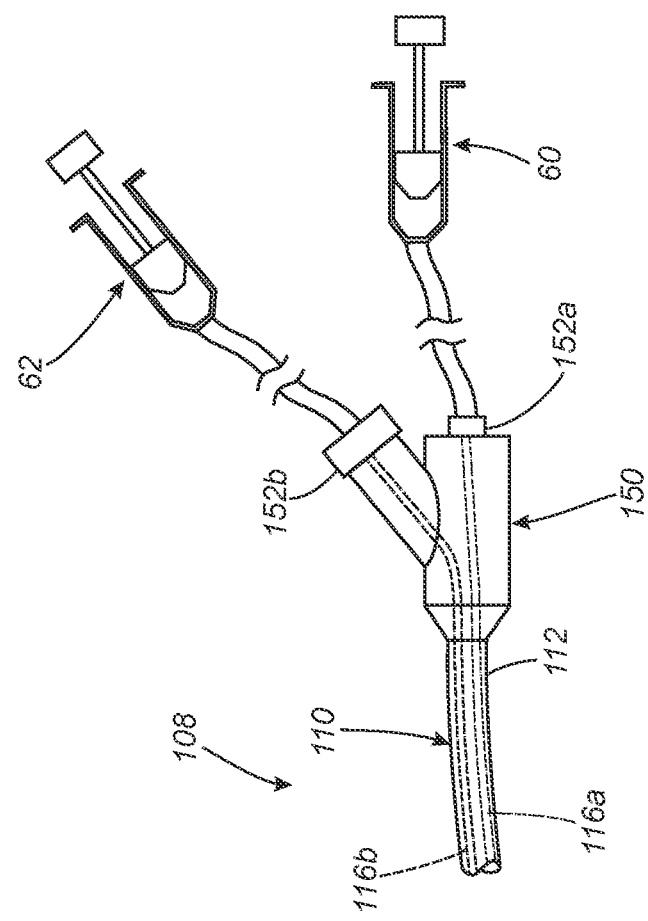
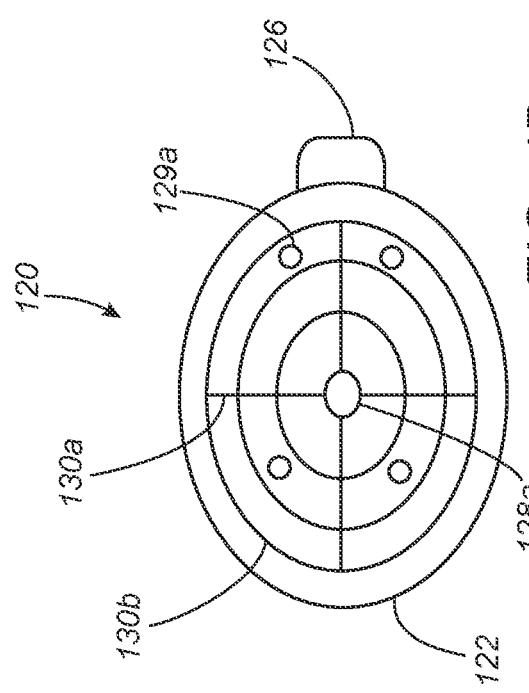
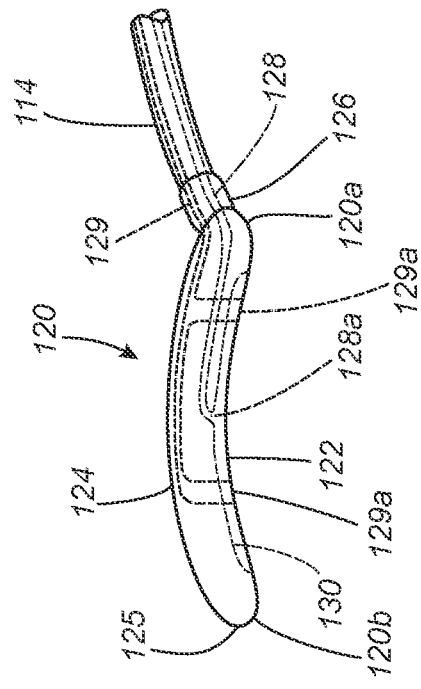
FIG. 4A
FIG. 4B

FLOW DISTRIBUTION PAD AND METHODS FOR USING THEM

RELATED APPLICATION DATA

This application claims benefit of provisional application Ser. No. 62/298,455, filed Feb. 22, 2016, the entire disclosure of which is expressly incorporated by reference herein.

FIELD OF THE INVENTION

The present invention relates generally to apparatus, systems, and methods for delivering fluids into a patient's body, and more particularly to apparatus, systems, and methods for delivering relatively low volumes of fluids to tissue or other body surfaces.

BACKGROUND

Topical medications and other liquids are frequently applied using absorbent swabs, pads, and/or sponges. Even for single applications, this can be a wasteful and/or imprecise method of agent delivery. In applications where continuous or repeated agent delivery is desired, this becomes even more problematic since, ideally, the flow rate for continuous application would be quite small but there is a need for consistent delivery and/or diffusion over a larger surface.

Therefore, apparatus and methods that facilitate delivering agents or fluids in a controlled manner would be useful.

SUMMARY

The present invention is directed to apparatus, systems, and methods for delivering fluids into a patient's body, and more particularly to apparatus, systems, and methods for delivering relatively low volumes of fluids to tissue or other body surfaces.

In accordance with one embodiment, an apparatus is provided for delivering fluids into a patient's body that includes a tubular member comprising a proximal end, a distal end sized for introduction into a patient's body, and a fluid delivery lumen extending between the proximal and distal ends; and a flexible pad on the distal end including a front or tissue contact surface, a passage communicating with the fluid delivery lumen, and plurality of capillary channels in the tissue contact surface communicating with the passage, the capillary channels configured to deliver fluid from the fluid delivery lumen and passage to tissue contacted by the tissue contact surface.

In accordance with another embodiment, a system is provided for delivering fluids into a patient's body that includes a tubular member comprising a proximal end, a distal end sized for introduction into a patient's body, and a fluid delivery lumen extending between the proximal and distal ends; a flexible pad on the distal end including a tissue contact surface, a passage communicating with the fluid delivery lumen, and plurality of delivery channels in the tissue contact surface communicating with the passage, the delivery channels configured to deliver fluid from the fluid delivery lumen and passage to tissue contacted by the tissue contact surface; and a source of fluid connectable to the proximal end of the tubular member for delivering the fluid through the fluid delivery lumen and along the delivery channels.

Optionally, the tubular member may include a vacuum lumen extending between the proximal and distal ends, and wherein the pad includes one or more vacuum ports in the front surface communicating with the vacuum lumen, the one or more vacuum ports being spaced apart from the delivery channels, and the system may further include a source of vacuum connectable to the proximal end of the tubular member for delivering a vacuum through the vacuum lumen to the vacuum ports.

In accordance with still another embodiment, a method is provided for delivering fluids into a patient's body that includes introducing a pad including a tissue contact surface and plurality of delivery channels in the tissue contact surface into a body passage; placing the tissue contact surface against a body surface adjacent the body passage such that open sides of the delivery channels contact the body surface; and delivering fluid into the pad such that the fluid flows along the delivery channels to distribute the fluid over a portion of the body surface.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which:

FIG. 1 is a side view of an exemplary embodiment of a fluid delivery device that includes a pad including recessed delivery channels for delivering fluid to a surface contacted by the pad.

FIG. 2A is a detail of a pad that may be included in the delivery device of FIG. 1.

FIG. 2B is a cross-section of the pad of FIG. 2A taken along plane 2B-2B.

FIGS. 3A-3D are end views of a tissue contact surface that may be included in a pad of a delivery device, showing exemplary embodiments of networks of delivery channels that may be provided in the tissue contact surface.

FIG. 4A is a side of another exemplary embodiment of a fluid delivery device that includes a pad including recessed delivery channels for delivering fluid to a surface contacted by the pad.

FIG. 4B is a view of a front surface of the pad of FIG. 4A.

DETAILED DESCRIPTION OF THE EXEMPLARY EMBODIMENTS

Turning to the drawings, FIGS. 1-2B shows an exemplary embodiment of a fluid delivery device 8 that includes an elongate catheter, shaft, or other tubular member 10 carrying a pad 20 including recessed delivery channels 30 for delivering fluid to a surface contacted by the pad 20, e.g., a tissue or other body surface 90 of a patient. Generally, the catheter 10 is an elongate tubular member including a proximal end 12, a distal end 14 sized for insertion into a patient's body, and one or more lumens 16 extending between the proximal and distal ends 12, 14, thereby defining a central longitudinal axis 18. For example, the catheter 10 may include an infusion lumen 16 that extends between the proximal and distal ends 12, 14, e.g., communicating with the delivery channels 30 in the pad 20, as described further below. Optionally, the catheter 10 may include one or more additional lumens, e.g., a vacuum lumen (not shown) to enhance securing the pad 20 to the body surface 90, as described further elsewhere herein.

The catheter 10 may be substantially flexible, semi-rigid, and/or rigid along its length, and may be formed from a variety of materials, including plastic, metal, and/or composite materials, as is well known to those skilled in the art. For example, in one embodiment, the catheter 10 may be semi-rigid or rigid at the proximal end 12 to enhance pushability and/or torquability of the catheter 10 without substantial risk of buckling or kinking. At the distal end, the catheter 10 may be flexible or semi-rigid, e.g., having sufficient column strength such that a distal force may be applied to the pad 20 from the proximal end 12, but may have some flexibility to accommodate insertion into an irregular passage, such as a patient's mouth, throat, gastrointestinal tract, and/or airway or through a port into a patient's thoracic cavity, abdomen and the like (not shown). Alternatively, the device may be placed or implanted subdermally, epidurally, or in other locations within the body. Further, Alternatively, the catheter 10 may be substantially flexible along its entire length or at least for a predetermined distance from the distal end 14 to facilitate advancement through one or more longer body passages, e.g., within a patient's vasculature. In another alternative, the catheter 10 may be malleable such that the catheter 10 may be bent to a desired shape when a predetermined threshold force is exceeded, which may be maintained until bent further, e.g., such that the catheter 10 may be arranged into a desired geometry based on the patient anatomy involved.

In an exemplary embodiment, the catheter 10 may include an inner liner at least partially or entirely surrounding or otherwise defining the infusion lumen 16, a reinforcement layer surrounding the inner liner, and an outer jacket surrounding the reinforcement layer (not shown), each of which may extend at least partially between the proximal and distal ends 12, 14 of the catheter 10. Optionally, the infusion lumen 16 may include lubricious material or may be formed from one or more layers of thermoplastic or other polymeric material including one or more coatings on the inner surface having desired properties, e.g., a hydrophilic and/or lubricious coating.

Returning to FIG. 1, a handle or hub 50 may be provided on the proximal end 12 of the catheter 10, e.g., configured and/or sized for holding and/or manipulating the device 8 from the proximal end 12. In addition, the handle 50 may include one or more ports, e.g., port 52 communicating with the infusion lumen 16, which may be coupled to a source of fluid, e.g., a syringe, container, and/or fluid line (not shown), as described further elsewhere herein. Optionally, the port 52 may include one or more valves or connectors, e.g., a Luer fitting, for removably connecting the source of fluid to the port 52.

With particular reference to FIGS. 2A and 2B, the pad 20 may be a generally planar or disc member including a front or tissue contact surface 22, a back surface 24 including a hub 26 or other feature for attaching the pad 20 to the distal end 14 of the catheter 10, and an outer perimeter 25 extending between the front and back surfaces 24, 26. In exemplary embodiments, the hub 26 may be coupled to the distal end 14 by one or more of an interference fit, e.g., by receiving one of the distal end 14 and the hub 26 in a recess in the other of the hub 26 and the distal end 14, by bonding with adhesive, fusing, sonic welding, insert molding, overmolding, and the like. The pad 20 also includes a passage 28 extending between the hub 26 and the front surface 22, e.g., communicating with the lumen 16 for delivering fluid from the lumen 16 to delivery channels 30 in the front surface 22.

As best seen in FIG. 2B, the delivery channels 30 may include a plurality of recesses formed in the front surface 22, e.g., having a desired cross-sectional shape to facilitate capillary action directing fluid along the delivery channels 30. For example, as shown in FIG. 2B, the delivery channels 30 may have a "U" shaped cross-section, e.g., with a rounded bottom wall 32, substantially vertical, straight side walls 34, and an open side 36 along the front surface 22. Alternatively, the delivery channels 30 may have other shapes, e.g., a "V" shaped cross-section, a partial circular or elliptical cross-section, e.g., such that the side walls define a generally circular or other curved arc, e.g., less than or greater than one hundred eighty degrees (180°) of a circle, or other cross-section. The delivery channels 30 may have a substantially uniform cross-sectional width, e.g., between the side walls 34, and/or depth, e.g., between the bottom wall 32 and the open side 36, e.g., having a maximum cross-sectional width or depth of not more than one or two millimeters (1.0-2.0 mm). Alternatively, the width and/or depth may be varied in different regions of the front surface 22, e.g., to promote fluid flow in a desired manner along the front surface 22.

The pad 20 may be substantially rigid, semi-rigid, or flexible, as desired, e.g., formed from plastic, metal or composite materials. For example, the pad 20 including the hub 26 may be integrally formed, e.g., molded, cast, and the like, from PEBAX, urethane, silicone, or other material. Optionally, the pad 20 may be formed at least partially from hydrophilic and/or lubricious material, e.g., over the front surface 22, which may enhance capillary action delivering fluid along the delivery channels 30. In another option, at least the walls of the delivery channels 30 may be coated with hydrophilic and/or lubricious material.

In one embodiment, the pad 20 may be formed from conformable material that maintains a predetermined shape when free from external forces, yet allows the front surface 22 to conform to contacted tissue, e.g., when a distal force is applied from the proximal end 12 of the catheter 10, as described elsewhere herein. The flexibility of the pad 20 may be substantially uniform along the front surface 22 or may be different in different regions, e.g., more rigid in the center, e.g., around the hub 26, and more flexible away from the hub 26, e.g., towards the outer perimeter 25. In an exemplary embodiment, the front surface 22 of the pad may be biased to one of a substantially flat, concave, or convex shape, which may be deformed when pressed against a contacted surface, e.g., to place the front surface 22 firmly against the contacted surface such that the delivery channels 30 are sealingly placed against the contacted surface, e.g., such that the contacted surface substantially seals the open end 36 of the delivery channels 30.

For example, in a relaxed state, the pad 20 may have a shallow cup shape, i.e., such that the front surface 22 has a shallow concave shape with a lip or rim (not shown) extending around the perimeter 25 adjacent the front surface 22. In one embodiment, the lip may define an outer channel (not shown) on the front surface 22 of the pad 20. Alternatively, one or more projections or features (not shown) may be provided on the pad 22 within the lip to divide the channel into smaller channels and/or prevent the channel from collapsing when the front surface 22 of the pad 20 is pressed against tissue. When the front surface 22 is pressed against a contacted surface, the lip may provide a seal around the perimeter 25, while the front surface 22 deforms to seal one or more of the delivery channels 30 against the contacted surface. In this manner, fluid introduced through the lumen 16 and passage 28 may reach the delivery channels 30 and spread along the delivery channels 30 outwardly towards the perimeter 25 of the pad 20, e.g., thereby applying the fluid and any agents therein to tissue of the contacted surface.

For example, as shown in FIG. 2A, the passage 28 includes an opening 28a at the front surface 22 and the delivery channels 30 may extend laterally and/or outwardly from the opening 28a. A relatively small volume of fluid may be introduced through the lumen 16 into the passage 28 such that the fluid pools at the opening 28a against the contacted surface. The fluid may then travel out into the delivery channels 30 along the contacted surface towards the perimeter 25 of the pad 30 to distribute the fluid over the contacted surface, where the fluid may be absorbed or otherwise delivered to tissue at or beneath the contacted surface.

In an exemplary embodiment, the fluid may include a topical anesthetic or other agent, which may be absorbed by the tissue, e.g., to expose the anesthetic to nerves adjacent the tissue. For example, the pad 20 may be placed in contact with the patient's skin or a mucosal surface, whereupon the anesthetic may be delivered to the front surface 22 and spread out along the delivery channels 30 and be absorbed by the tissue, e.g., to block the underlying nerves. In exemplary embodiments, a relatively small volume of fluid may be delivered, e.g., between about one to five milliliters (1.0-5.0 mL), which may be sufficient to flow out through the delivery channels 30 to deliver sufficient dosage of anesthetic or other agent to the tissue. Optionally, a procedure may be performed at or adjacent the contacted tissue, e.g., after removing the pad 20 or while the agent is intermittently or continuously introduced through the lumen 16 to the delivery channels 30. Once sufficient fluid has been delivered or the procedure is completed, the device 8 may be removed.

Turning to FIG. 3A, an exemplary embodiment of a network of delivery channels 30 is shown. In this embodiment, the front surface 22 of the pad has an elliptical or other oblong shape around the perimeter 25, i.e., with a length greater than its width. In an exemplary embodiment, the pad 20 may have a width between about two and thirty millimeters (2.0-30 mm), e.g., about 0.2 inch (5.0 mm), and a length between about ten and fifty millimeters (10-50 mm), e.g., approximately one inch (25.0 mm). Alternatively, the front surface 22 may have other shapes, e.g., a substantially circular shape, a rounded square or rectangular shape, and the like. In addition, as shown, the delivery channels 30 may be arranged to include a plurality of radial channels 32 that communicate with the opening 28a and extend outwardly away from the opening 28a towards the perimeter 25, and a plurality of circumferential channels 34 that communicate with the radial channels 32 and extend circumferentially, e.g., in circular or oblong paths concentric to the outer perimeter 25, to distribute fluid from the opening 28a through the radial and circumferential channels 32, 34 over a portion of the front surface 22. In this manner, fluid delivered to the opening 28a may travel outwardly by capillary action through the radial channels 32 and the circumferential channels 34 to distribute the fluid over and/or into tissue at the contacted surface.

Alternatively, as shown in FIG. 3B, a pad 20' is shown that includes a pair of openings 28a' spaced apart from one another on the front surface 22.' For example, a single passage (not shown) may extend from the hub (also not shown) of the pad 20' and divide to communicate with both openings 28a.' Each opening 28a' may include a network of delivery channels 30' including radial channels 32' and circumferential channels 34'. As shown, the network of channels 30' from each opening 28a' may interconnect and/or otherwise communicate with each other, which may enhance distribution of fluid over the front surface 22.'

Alternatively, each opening 28a' may include an independent network of delivery channels (not shown), e.g., isolated from the other network, for delivering fluid along respective regions of the front surface 22.' In this embodiment, the front surface 22' has an oblong shape, as shown, although the front surface 22' may have other shapes, as desired. Although two openings 28a' are shown in FIG. 3B, it will be appreciated that any desired number of openings and corresponding networks of delivery channels may be provided on the pad.

In another alternative, shown in FIG. 3C, a pad 20" is shown that includes a network of channels 30" including radial channels 32" that extend orthogonal to one another outwardly towards the perimeter 25," e.g., vertically and horizontally from the opening 28a," and lateral channels 34" that extend orthogonally from the radial channels 32." In still another alternative, shown in FIG. 3D, another pad 20''' is shown that includes a network of delivery channels 30''' that extend outwardly from an opening 28a''' in a random pattern, e.g., including a plurality of channels 30''' that extend at least partially radially and circumferentially outwardly towards the perimeter 22'''.

Turning to FIGS. 4A and 4B, another embodiment of a fluid delivery device 108 is shown that includes an elongate catheter, shaft, or tubular member 110 carrying a pad 120 including recessed delivery channels 130 in a front surface 122 thereof for delivering fluid to a surface contacted by the pad 120, generally similar to the previous embodiment. The catheter 110 also includes an infusion lumen 116a communicating between a first port 152a in the handle 150 (connectable to a source of fluid 60) and a passage 128 extending from a hub 126 on a first end 120a of the pad 120 to an opening 128a in the front surface 122 that communicates with the delivery channels 130, also similar to the previous embodiment, such that the delivery channels 130 extend partially between the first end 120a and a second opposite end 120b of the pad 120 without extending entirely to the second end 120b. In addition to the infusion lumen 116a, the catheter 110 also includes a second lumen 116b extending between the proximal and distal ends 112, 114 of the catheter 110, e.g., from a second port 152b in the handle 150 to a second passage 129 in the hub 126 and pad 120.

The second port 152b may be coupled to a source of vacuum, e.g., a syringe, vacuum line, and the like 62 for enhancing engagement of the front surface 122 with a tissue or other contacted surface (not shown). For example, the second passage 129 may communicate with one or more vacuum ports 129a in the front surface 122, e.g., a plurality of vacuum ports 129a spaced apart around the front surface, that are substantially spaced apart or otherwise isolated from the delivery channels 130. Thus, when the front surface 122 is pressed against a contacted surface and a vacuum is applied to the second lumen 116b and passage 129, the vacuum may be applied to the vacuum ports 129a, thereby engaging the front surface 122 against the contacted surface. Fluid may then be delivered via the delivery channels 130, similar to the previous embodiment, to distribute the fluid over the contacted surface and/or into tissue underlying the contacted surface.

Such vacuum ports 129a in the front surface 122 may be particularly useful if the pad hub 126 extends from the perimeter 125 of the pad 120, rather from the back surface 124, since a distal force applied from the proximal end 112 of the catheter 110 may not be effective in pressing the front surface 122 against a desired surface. Optionally, the flexibility of the pad 120 may be varied over the front surface 122, e.g., more rigid on the end 120a closer to the hub 126 and more flexible on the opposite end 120b. In this option, the vacuum ports 129a may allow the flexible region to be pulled against and/or conform to a tissue surface, which may enhance delivery of fluid to the tissue.

During use, the device 8 or 108 may be introduced into a body passage to direct the front surface 22, 122 of the pad 20, 120 against a target tissue or bodily surface to allow a relatively small volume of fluid to be delivered and/or to allow fluid to be delivered slowly, e.g., intermittently or substantially continuously, in order to treat the tissue and/or to prepare the tissue for a subsequent procedure, e.g., a diagnostic and/or therapeutic procedure. During introduction, the pad 20, 120 may remain in its relaxed, e.g., generally planar or concave, orientation, if the bodily passage is sized to accommodate the pad 20, 120.

Alternatively, the pad 20, 120 may be compressed, e.g., rolled or folded, into a contracted state to facilitate introduction into a smaller bodily passage. For example, an introducer sheath or other tubular body (not shown) may be provided that is sized to be introduced into a target region that includes a lumen therein. The pad 20, 120, in its contracted state, may be sized to be received within the lumen of the introducer sheath and advanced therethrough into the target region, whereupon the pad 20, 120 may be deployed. Once deployed, the pad 20, 120 may assume its original orientation, and the front surface 22, 122 may be directed towards a desired surface at the target region and fluid may be introduced, similar to the methods described above.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

Further, in describing representative embodiments, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. An apparatus for delivering fluids into a patient's body, comprising:
  a tubular member comprising a proximal end, a distal end sized for introduction into a patient's throat, a handle or hub on the proximal end configured for holding and manipulating the tubular member, and a fluid delivery lumen extending between the proximal and distal ends; and
  an elongate flexible pad defining a length between a first end and a second end thereof and including a pad hub on the first end connected to the distal end of the tubular member, the pad and pad hub integrally molded from the same material, the pad including a tissue contact surface extending from the first end along the length to the second end, and a back surface extending from the first end to the second end opposite the tissue contact surface, the tissue contact surface biased to a concave shape, a passage communicating with the fluid delivery lumen, and a plurality of delivery channels formed in the tissue contact surface communicating with the passage and extending from the first end along the tissue contact surface partially towards the second end without extending entirely to the second end, each delivery channel having side walls on opposite sides of an open side extending along the tissue contact surface and a bottom wall, the delivery channels configured to deliver fluid from the fluid delivery lumen and passage to tissue contacted by the tissue contact surface,
  wherein the tubular member has sufficient column strength such that a distal force may be applied to the pad from the proximal end and has flexibility to accommodate insertion into a patient's throat.

2. The apparatus of claim 1, wherein the delivery channels have one of a "U" and "V" shaped cross-section.

3. The apparatus of claim 1, wherein the delivery channels have a maximum cross-sectional width of not more than two millimeters such that fluid flows along the recesses by capillary action.

4. The apparatus of claim 1, wherein the passage includes an opening at the tissue contact surface and wherein at least some of the delivery channels extend outwardly away from the opening along the tissue contact surface towards an outer periphery of the pad to distribute fluid from the opening along the delivery channels over a portion of the tissue contact surface.

5. The apparatus of claim 1, wherein the pad is formed from conformable material that allows the tissue contact surface to conform to contacted tissue.

6. The apparatus of claim 1, wherein the tubular member further comprises a vacuum lumen extending between the proximal and distal ends, and wherein the pad includes one or more vacuum ports in the tissue contact surface communicating with the vacuum lumen, the one or more vacuum ports being spaced apart from the delivery channels.

7. The apparatus of claim 1, wherein the pad has an outer perimeter extending between the tissue contact surface and a back surface of the pad.

8. The apparatus of claim 7, wherein the outer perimeter defines one of a circular and an oblong shape.

9. The apparatus of claim 1, wherein the tubular member is semi-rigid or rigid at the proximal end to enhance pushability of the distal end from the proximal end.

10. The apparatus of claim 1, wherein the pad is configured to be compressed into a contracted state to facilitate introduction into a body passage, and biased such that, when the pad is deployed at a target region, the tissue contact surface assume its original substantially flat, convex, or concave shape such that the tissue contact surface may be directed towards a desired surface at the target region.

11. The apparatus of claim 1, wherein the pad is sized to be introduced into a patient's mouth or throat.

12. The apparatus of claim 1, wherein the pad is formed from a single layer of material between the tissue contact surface and the back surface.

13. A apparatus for delivering fluids into a patient's body, comprising:
  a tubular member comprising a proximal end, a distal end sized for introduction into a patient's throat, a handle or hub on the proximal end configured for holding and manipulating the tubular member, and a fluid delivery lumen extending between the proximal and distal ends; and a flexible pad including a pad hub on a first end of the pad connected to the distal end of the tubular member, the pad and pad hub integrally molded from the same material, the pad including a tissue contact surface extending from the first end to a second end opposite the first end, the tissue contact surface biased to a concave shape, a passage communicating with the fluid delivery lumen, and a plurality of delivery channels formed in the tissue contact surface communicating with the passage and extending from the first end along the tissue contact surface towards the second end, each delivery channel having side walls on opposite sides of an open side extending along the tissue contact surface and a bottom wall, the delivery channels configured to deliver fluid from the fluid delivery lumen and passage to tissue contacted by the tissue contact surface, wherein the tubular member has sufficient column strength such that a distal force may be applied to the pad from the proximal end and has flexibility to accommodate insertion into a patient's throat, wherein the passage includes an opening at the tissue contact surface and wherein at least some of the delivery channels extend outwardly away from the opening along the tissue contact surface towards an outer periphery of the pad to distribute fluid from the opening along the delivery channels over a portion of the tissue contact surface, and wherein the delivery channels include a plurality of radial channels that communicate with the opening and extend outwardly away from the opening and a plurality of circumferential or lateral channels that communicate with the radial channels to distribute fluid by capillary action from the opening through the radial and the circumferential or lateral channels over a portion of the tissue contact surface.

14. A system for delivering fluids into a patient's body, comprising:

a tubular member comprising a proximal end, a distal end sized for introduction into a patient's body, a handle or hub on the proximal end configured for holding and manipulating the tubular member, and a fluid delivery lumen extending between the proximal and distal ends;

an elongate flexible pad defining a length between a first end and a second end thereof and including a pad hub integrally molded on the first end and connected to the distal end of the tubular member, the pad including a tissue contact surface extending from the first end along the length to the second end, and a back surface extending from the first end to the second end opposite the tissue contact surface, the tissue contact surface biased to a concave shape, a passage communicating with the fluid delivery lumen, and a plurality of open delivery channels formed in the tissue contact surface communicating with the passage and extending from the first end along the tissue contact surface partially towards the second end without extending entirely to the second end, the delivery channels configured to deliver fluid from the fluid delivery lumen and passage to tissue contacted by the tissue contact surface; and a source of fluid connectable to a port on the handle or hub for delivering the fluid through the fluid delivery lumen and along the delivery channels, wherein the tubular member has sufficient column strength such that a distal force may be applied to the pad from the proximal end and has flexibility to accommodate insertion into a patient's throat.

15. The system of claim 14, the port and source of fluid comprising cooperating connectors for coupling the source of fluid to the port.

16. The system of claim 14, wherein the tubular member further comprises a vacuum lumen extending between the proximal and distal ends, and wherein the pad includes one or more vacuum ports in the tissue contact surface communicating with the vacuum lumen, the one or more vacuum ports being spaced apart from the delivery channels.

17. The system of claim 16, further comprising a source of vacuum connectable to the proximal end of the tubular member for delivering a vacuum through the vacuum lumen to the vacuum ports.

18. The system of claim 14, wherein the fluid comprises a topical anesthetic.

19. An apparatus for delivering fluids into a patient's body, comprising:

a tubular member comprising a proximal end, a distal end sized for introduction into a patient's body, a handle or hub on the proximal end configured for holding and manipulating the tubular member, and a fluid delivery lumen extending between the proximal and distal ends; and an elongate flexible pad defining a length between a first end and a second end and comprising a pad hub integrally formed on the first end coupled to the distal end of the tubular member, the pad including a tissue contact surface extending from the first end to the second end, and a back surface extending from the first end to the second end opposite the tissue contact surface, the tissue contact surface biased to a concave shape, a passage through the pad hub communicating with the fluid delivery lumen, and one or more elongate recessed delivery channels formed in the tissue contact surface communicating with the passage, each delivery channel including an open side wall extending from the first end along the tissue contact surface partially towards the second end without extending entirely to the second end, the one or more delivery channels configured to deliver fluid from the fluid delivery lumen and passage to tissue contacted by the tissue contact surface, wherein the tubular member has sufficient column strength such that a distal force may be applied to the pad from the proximal end and has flexibility to accommodate insertion into a patient's throat.

20. The apparatus of claim 19, wherein the pad further comprises a back surface opposite the tissue contact surface.

21. The apparatus of claim 19, wherein the pad is sized to be introduced into a patient's mouth or throat.

22. The apparatus of claim 19, wherein each delivery channel includes side walls on opposite sides of an open side extending along the tissue contact surface.

23. The apparatus of claim 22, wherein each delivery channel includes a bottom wall opposite the open side.

24. The apparatus of claim 22, wherein each delivery channel defines one of a "U" and "V" shaped cross-section.

25. The apparatus of claim 19, further comprising a port on the proximal end of the tubular member for connecting to a fluid source, the port communicating with the fluid delivery lumen for delivering fluid from the fluid source through the fluid delivery lumen, passage, and the one or more delivery channels to deliver the fluid along the tissue contact surface.

* * * * *